United States Patent [19]
Klein et al.

[11] 4,299,667
[45] Nov. 10, 1981

[54] PROCESS FOR RECOVERING PURE BENZENE

[75] Inventors: Helmut Klein, Hanau; Kamar P. John, Bad Homburg, both of Fed. Rep. of Germany

[73] Assignee: Metallgesellschaft Aktiengesellschaft, Frankfurt, Fed. Rep. of Germany

[21] Appl. No.: 172,728

[22] Filed: Jul. 28, 1980

[30] Foreign Application Priority Data

Jul. 31, 1979 [DE] Fed. Rep. of Germany ....... 2931012

[51] Int. Cl.$^3$ .......................... B01D 3/10; B01D 3/40
[52] U.S. Cl. ...................................... 203/42; 203/58; 203/75; 203/77; 203/78; 203/80; 203/82; 203/84; 203/93; 203/94; 585/808; 585/833; 585/857; 585/860; 585/862; 585/865
[58] Field of Search .............. 585/804, 807, 808, 833, 585/856, 857, 860, 862, 865; 208/308, 326, 313, 316, 321, 322, 325, 330, 331, 332, 333; 203/57, 58, 59, 62, 71, 72, 75, 77, 78, 80, 82, 84, 91, 93, 42, 94

[56] References Cited
U.S. PATENT DOCUMENTS 2,842,484  7/1958  Fleck .................................. 208/313
4,070,408  1/1978  Vickers ............................... 585/804

*Primary Examiner*—Frank Sever
*Attorney, Agent, or Firm*—Sprung, Felfe, Horn, Lynch & Kramer

[57] ABSTRACT

A process for recovering pure benzene from hydrocarbon mixtures containing the same and non-aromatic compounds which are gaseous and difficultly condensible is described in which the feedstock is fed to an initial distillation column operated at atmospheric or sub-atmospheric pressure. Overhead comprising benzene and non-aromatics is obtained and a portion thereof condensed. The condensible material is in part returned to the distillation column and in part subjected to extractive distillation to recover pure benzene. Those components which did not condense, i.e. the non-condensible and difficultly condensible components and entrained aromatics are fed to a reflux vessel such as a scrubber, stripper, or the like for recovery of any benzene or other valuable components which might be soluble in a selective solvent and used for such recovery. The selective solvent can be the same solvent used for the extractive distillation.

4 Claims, 1 Drawing Figure

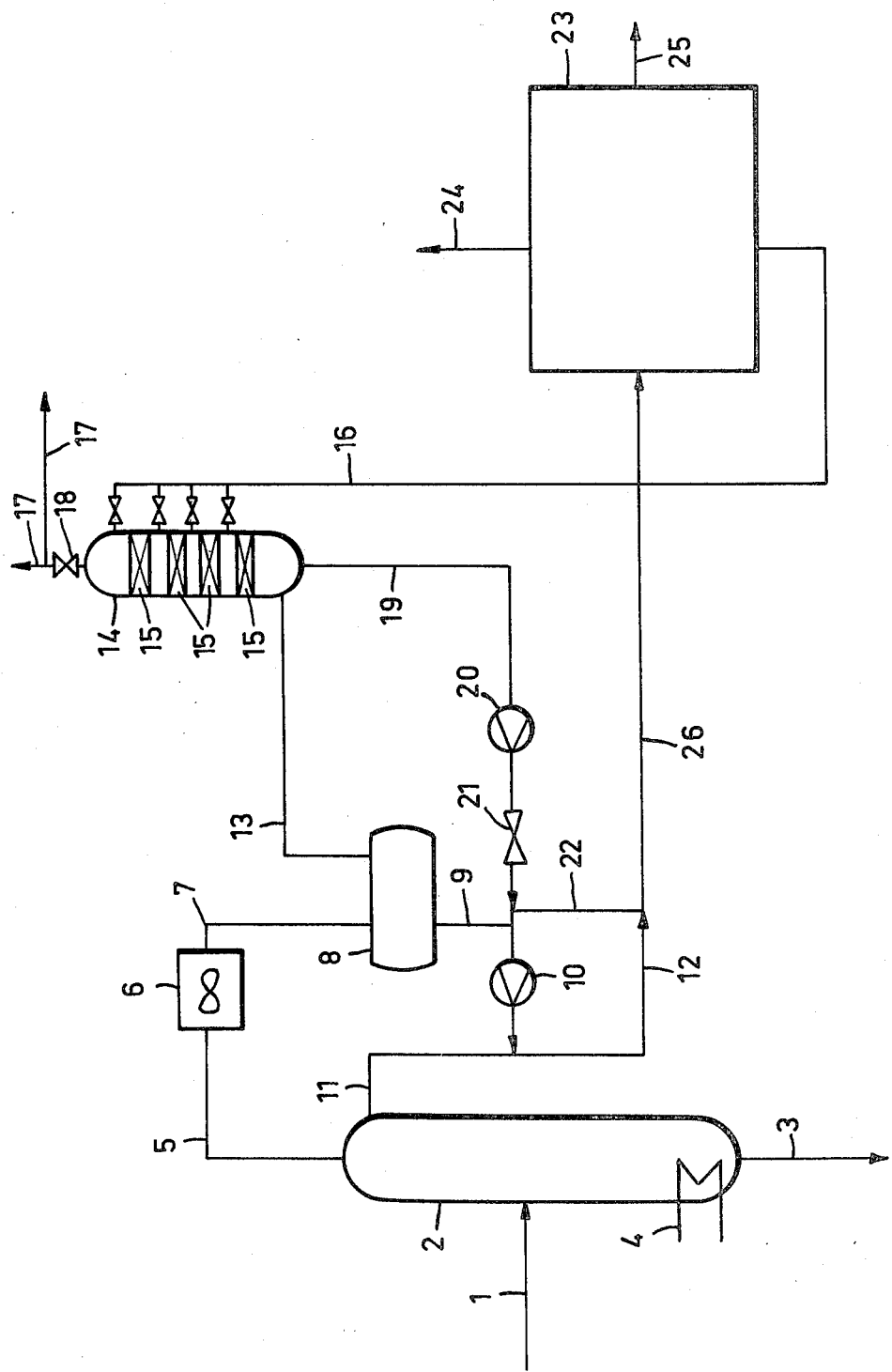

PROCESS FOR RECOVERING PURE BENZENE

BACKGROUND OF THE INVENTION

1. Field of the Invention

This invention relates to a process of recovering pure benzene from mixed hydrocarbons containing the same and gaseous and difficultly condensible nonaromatic compounds, by extractive distillation with a selective solvent.

2. Discussion of Prior Art

For a recovery of pure aromatic compounds from mixed hydrocarbons by extractive distillation with a selective solvent it is known to feed the feedstock to be separated to a stabilizing column, which precedes the distillation column, to withdraw a high-boiling residue from the sump of the stabilizing column and to withdraw mixed vapors of aromatic and nonaromatic compounds from the stabilizing column at its lower part or some plates above its inlet for the feedstock to be separated. To control the evaporation conditions, the mixture is then fed in the form of a vapor or in an entirely or partly liquefied form to an extractive distillation column at one or more points and the pure aromatic compounds together with the selective solvents are withdrawn from the sump of the extractive distillation column and subsequently separated (see German Offenlegunsschrift No. 2,263,344).

In another known process of recovering pure aromatic hydrocarbons by extractive distillation with a selective solvent, the benzene and toluene fractions are simultaneously withdrawn as overhead vapors from a pretreating column and as a vapor are supplied to an extractive distillation column.

The nonaromatic compounds are withdrawn as an overhead product and the extraction solvent together with benzene and toluene is withdrawn from the sump of the extractive distillation column, which is succeeded by a stripping column. The extracting solvent is thus separated from benzene and toluene in the stripping column and becomes as a sump product. The benzene and toluene, which become available as overhead products, from the stripping column, may subsequently be separated in known manner by distillation, if desired (German Offenlegungsschrift No. 2,313,773).

When the nonaromatic compounds have an initial boiling point of about 30° C., extractive distillation with the aid of the solvent may be used for an exact separation into nonaromatic compounds and pure benzene. But owing to the low boiling point of the low-boiling nonaromatic component, the extractive distillation column must be operated under superatmospheric pressure so that all temperatures are increased and a heat exchange between hot solvent from the sump of the stripping column and the sump product of the extractive distillation column can no longer be effected.

In such cases the feedstock is prepurified with the solvent in a preceding extractive distillation column, which is operated under such superatmospheric pressure that its overhead product consisting of the low-boiling components of the feedstock condenses at a temperature which permits an economical condensation of the overhead product. That extractive distillation is so controlled that no benzene is lost in the overhead product. It is not endeavored to obtain by said extractive distillation a sump product consisting of solvent and benzene. On the contrary, all nonaromatic compounds having an initial boiling point at 60° or 65° C. are also collected in the sump.

The feedstock is then separated into nonaromatic compounds or raffinate and pure benzene (extract) in a succeeding second extractive distillation effected by means of the solvent. That second extractive distillation is effected under a slightly subatmospheric pressure so that the heat of the hot solvent from the sump of the stripping column can be fully utilized for heating the second extractive distillation column and also for heating the first extractive distillation column because the latter may be supplied with solvent at a very low rate so that its sump temperature is so low that an effective heat exchange is possible.

That process cannot be used for an economical recovery of pure benzene if the feedstock consists of components which can be condensed only with very great difficulty, i.e., when part of the feedstock is gaseous under atmospheric pressure.

Those components which remain gaseous or are difficultly condensible can be condensed only under very high pressure or with the aid of a refrigerant. A sufficiently high pressure involves a great increase of the distillation temperatures so that high-pressure steam or tubular heaters must be used to generate the heat required for distillation. In that case the removal of the low-boiling hydrocarbons is controlled by a pressure-regulating valve so that the gaseous state is resumed in most cases after the pressure regulation. This may involve a loss of benzene to be recovered.

OBJECTS OF THE INVENTION

It is an object of the invention to avoid these and other disadvantages of the known processes and to provide for the recovery of pure benzene an economical process which is suitable also for a treatment of feedstocks that contain components which are gaseous under atmospheric pressure.

SUMMARY OF THE INVENTION

This object is accomplished in that the mixed hydrocarbons containing non-condensible or difficultly condensible non-aromatics and benzene are supplied to a column in which atmospheric pressure or a slightly subatmospheric pressure is maintained, the impurities and higher-boiling hydrocarbons are withdrawn from the sump of the column, an overhead product is withdrawn from the column and is cooled to temperatures between 40° and 80° C. to obtain a liquid condensate consisting of benzene and non-aromatic compounds. The non-condensible difficultly condensible components and entrained benzene are discharged and preferably fed to a reflux vessel, e.g. a scrubber or spray condenser to which extractive solvent can be added to recover benzene from the gases. Part of the liquid condensate consisting of benzene and non-aromatic compounds is refluxed to the column while another part of said condensate is fed to a succeeding extractive distillation column and processed therein for a recovery of pure benzene. The gaseous non-condensibles and difficult condensibles and eintrained benzene are contacted with counterflowing selective solvent to dissolve the soluble components including benzene completely from the gas phase. The mixture consisting of solvent and benzene is supplied to the extractive distillation column and processed for recovery of pure benzene. A portion of such mixture of solvent and benzene can be returned to the top of the initial distillation column where the solvent will function as the solvent of an extractive distillation column.

Within the scope of the invention, a reflux ratio of 0.1:1 is preferably maintained for the refluxing of part of the liquid condensate consisting of benzene and non-aromatic compounds to the column.

According to a preferred further feature of the invention the gas phase is contacted with the selective solvent in a spray condenser.

Also within the scope of the invention, the gas phase may be contacted with the selective solvent in a scrubber rather than a spray condenser.

Within the scope of the invention, the gas phase may alternatively be contacted with the selective solvent in an exhaust gas cooler.

According to a preferred further feature of the invention the gas phase is cooled with cold solvent.

If, within the scope of the invention, a conventional exhaust gas cooler is used to scrub the gas phase, that cooler is preferably horizontal and one or more exchange tubes in the upper cooling zone consist desirably of spray tubes.

Additional advantages afforded by the invention reside in that the heat requirement of the first column is very small and an optimum heat exchange is permitted in the succeeding extractive distillation column. This reduces the steam requirement to about 0.5 ton of steam per ton of recovered pure benzene.

Extractive distillation solvents which can be used in the process of the invention include: N-methylpyrrolidone, N-formylmorpholane, aniline, sulfolane, dimethylsulfoxide, and other solvents higher boiling than the aromatics to be recovered.

The volume ratio of extractive distillation solvent to material to be extractively distilled out of the gaseous phase of the top product of column 2 is 1–7 volumes solvent per volume of material to be recovered out of the said gaseous phase, preferably 2 to 5:1.

The volume ratio of solvent in the scrubber or spray condenser or exhaust gas cooler is preferably 1–7 volume solvent per volume of the condensible component (for example benzene) in the gaseous phase, preferably 2–5:1.

The pressure in the initial distillation vessel which is normally not an extractive distillation column, is 1.0 to 1.5 atmospheric pressure but pressures down to 380 Torr can be employed. The column top temperature is between 80° and 60° C.

When the overhead (=100%) is condensed between 90 and 100 percent, preferably 8 and 10 percent is refluxed back to the column while between 10 and 0 percent, preferably 9 and 3 percent is fed to the scrubber or spray condenser or exhaust gas cooler.

The scrubber spray column is operated at a temperature of 50° to 55° C. and a pressure of 385 Torr to 1.2 atmospheres. Preferably the pressure is 0.5 to 1.1 atmospheres absolute.

The recovered liquid distillate from column 2 and scrubber or spray condenser or exhaust gas cooler is fed to an existing extractive distillation unit directly.

Generally the extractive distillates provide benzene as extract of exceptional purity, e.g. at least 99.99 percent pure. This distillation also provides as raffinate the total amount of non-aromatics contained in the feed to the extractive distillation unit 23 (line 26) and 1 to 10% of benzene.

The gaseous and difficultly condensible non-aromatic compounds to which this invention is directed included the following: inerts like nitrogene, low boilers like $C_2$—, $C_3$—, $C_4$—, $C_5$—hydrocarbons and entrained aromatics in the gaseous phase like preferable benzene and mixtures thereof.

Their boiling point is generally −90° C. to +80° C. at atmospheric pressure.

Owing to the low operating costs and the low equipment expenditure, the novel process is highly economical.

BRIEF DESCRIPTION OF THE DRAWING

The invention is diagrammatically illustrated by way of example employing the annexed drawing which is a flow diagram. The same is now described more in detail.

DESCRIPTION OF SPECIFIC EMBODIMENT

In inlet 1 for feedstock (mixed $C_4/C_5$—hydrocarbons, non-aromatic compounds, benzene and higher-boiling compounds), a column (rerun column) 2, an outlet 3 for sump product (higherboiling compounds); a reboiler 4, an outlet 5 for the overhead product of column 2, a condenser 6, a conduit 7 leading to a reflux vessel 8, a conduit 9 for liquid from 8, a pump 10, a reflux conduit 11 leading to the top of column 2, a conduit 12 for feeding feedstock to an extractive distillation plant 23, a gas outlet 13, a scrubber 14 (or spray condenser or exhaust gas cooler), filled with layers of Raschig rings 15, a conduit 16 for supplying cold solvent, an outlet 17 from the scrubber or spray condenser or exhaust gas cooler 14, pressure-regulating valve 18, an outlet 19 for withdrawing benzene and solvent from the lower part of the scrubber or spray condenser or exhaust gas cooler 14, a pump 20, a level control valve 21, a conduit 22 together with conduit 12 via conduit 26 to an extractive distillation plant 23, an outlet 24 for the raffinate, an outlet 25 for pure benzene, the extract.

The process is carried out as follows:

The mixed feedstocks are fed through 1 to a conventional rerun column 2, which is provided with a reboiler 4 and operated under an overhead pressure of 1 bar and at a sump temperature of 95° C. High-boiling product formed by hydrogenation is withdrawn from the sump through 3. The overhead product is withdrawn through 5 and is condensed at a temperature of about 75° C. in condenser 6 and fed at about 55° through 7 into the reflux vessel 8, in which a liquid phase and a gas phase are formed.

The liquid phase consists of benzene and the non-aromatic compounds, which have an initial boiling point at about 60° C., and is refluxed in part to the column 2 through conduit 9, pump 10 and conduit 11 whereas another part is fed to plant 23 as mixed feedstocks. The reflux ratio is 0.1:1. The gas phase is withdrawn from the reflux vessel 8 through 13 and fed to the scrubber or spray condenser or exhaust gas cooler 14, which is filled with Raschig rings, which form a plurality of packed layers 15. Preferably, the Raschig rings consist of stainless steel and have a size of 25×25 mm. Stainless steel turnings may be alternatively used. Each packed layer is about 500 to 800 mm high. Four packed layers are provided. Inlets 16 provided between the layers are used to feed cold solvent, such as N-methylpyrrolidone, in such a manner that it is well distributed over the layers. The gas phase is fed from the reflux vessel 8 through pipe 13 to the lower end thereof. The outlet 17 is mounted at the top of the scrubber or spray condenser or exhaust gas cooler 14 and connected to the latter through a pressure-regulating valve 18. Benzene and solvent are withdrawn from the lower part of 14 through 19, 20, 21, 22 and 26 and are fed under a level control to the extractive distillation plant 23. As a result, column 2 can be operated under a low pressure, condenser 6 can be operated so that the non-aromatic compounds boiling at or above 60° C. can be condensed in the presence of a gas, and the high proportion of benzene contained in the exhaust gas owing to the partial pressure conditions can be recovered in the succeeding scrubber or spray condenser or exhaust gas cooler 14, which is supplied with cold solvent via 16. The off-gas leaving the unit via conduit 17 consists out of the inserts and low-boiling hydrocarbons.

The heat exchange in the extractive distillation column 23 is effected in a conventional manner. The column 2 may be heated with waste heat from the extractive distillation plant 23. Raffinate and pure benzene are recovered from the extractive distillation plant 23 through 24 and 25, respectively.

Data relating to a numerical example are compiled in the following table (HC=hydrocarbons).

| Flow Rates in Conduits in kg/h (numerical Example Composition) | | | | | |
|---|---|---|---|---|---|
| Conduit | $C_3$— to $C_5$—HC | $C_6C_7$—HC | Benzene | High-boiling components | Solvent | Total |
| 1 | 153 | 13519 | 11168 | 400 | — | 25240 |
| 3 | — | — | 3 | 400 | — | 403 |
| 5 | 153 | 14793 | 12222 | — | — | 27168 |
| 9 | — | 14763 | 12205 | — | — | 26968 |
| 11 | — | 1274 | 1057 | — | — | 2331 |
| 12 | — | 13489 | 11148 | — | — | 24637 |
| 13 | 153 | 30 | 17 | — | — | 200 |
| 16 | — | — | — | — | 800 | 800 |
| 17 | 153 | — | — | — | — | 153 |
| 22 | — | 30 | 17 | — | 800 | 847 |
| 24 | — | 13519 | 165 | — | — | 13684 |
| 25 | — | — | 11000 | — | — | 11000 |
| 26 | — | 13519 | 11165 | — | 800 | 25484 |

What is claimed is:

1. A process for recovering benzene from a mixture of the same with gaseous and difficultly condensible non-aromatic compounds which comprises
   (A) distilling said mixture at atmospheric or reduced pressure to distill over benzene, and said non-aromatic compounds and to obtain impurities and higher boiling components as a sump product;
   (B) cooling said overhead from Step A to temperatures of 40° to 80° C. and producing a condensate containing benzene, returning a first position of said condensate to the distillation of step A;
   (C) feeding a second portion of said condensate from step B to an extractive distillation zone and therein extractively distilling said second portion to obtain pure benzene;
   (D) feeding the non-condensed components from step B to a scrubbing zone and therein contacting the same with counter-flowing selective solvent to remove benzene from said non-condensed components and removing a mixture comprising said selective solvent and benzene from said scrubbing zone and feeding said mixture to the distillation of step A or the extractive distillation zone of step C.

2. A process according to claim 1, wherein the extraction distillation of step C is performed to obtain as a stream thereof one in which a major component thereof is the extractive solvent which extractive solvent is employed as the selective solvent of step D.

3. A process according to claim 1, wherein the condensate obtained in step B is refluxed back to the distillation of step A at a reflux ration of 0.1:1.

4. A process according to claim 1, wherein the gas phase of step D is cooled with cold solvent.

* * * * *